United States Patent
Heider et al.

(10) Patent No.: US 6,841,301 B2
(45) Date of Patent: Jan. 11, 2005

(54) FLUOROALKYL PHOSPHATES FOR USE IN ELECTROCHEMICAL CELLS

(75) Inventors: Udo Heider, Riedstadt (DE); Michael Schmidt, Seeheim-Jugenheim (DE); Andreas Kühner, Darmstadt (DE); Peter Sartori, Utting (DE); Nikolai Ignatyev, Duisburg (DE)

(73) Assignee: Merck Patent GmbH, Darmstadt (DE)

( * ) Notice: Subject to any disclaimer, the term of this patent is extended or adjusted under 35 U.S.C. 154(b) by 101 days.

(21) Appl. No.: 09/918,464

(22) Filed: Aug. 1, 2001

(65) Prior Publication Data

US 2002/0022182 A1 Feb. 21, 2002

(30) Foreign Application Priority Data

Aug. 4, 2000 (DE) .......................................... 100 38 858

(51) Int. Cl.[7] .................. H01M 6/16; H01M 10/40; H01G 9/035; C07F 9/035; C01B 25/26
(52) U.S. Cl. .................. 429/199; 429/307; 429/345; 252/62.2; 423/301; 423/323; 568/16; 361/503; 361/504; 361/505
(58) Field of Search .................. 429/199, 307, 429/345; 252/62.2; 423/301, 323; 568/16; 361/503–505

(56) References Cited

U.S. PATENT DOCUMENTS 6,210,830 B1 4/2001 Sartori et al.

6,423,454 B1 7/2002 Heider et al.
2002/0001755 A1 * 1/2002 Heider et al.
2002/0012850 A1 * 1/2002 Schmidt et al.
2002/0015884 A1 * 2/2002 Schmidt et al.

OTHER PUBLICATIONS

Chan et al. ("Trifluoromethyl–substituted fluorophosphates and fluoroarsenates", Canadian Journal of Chemistry, vol. 46 (1968), pp. 1237–1248), no month.*

Chemical Abstract for Pavlenko et al. "Reaction of tris(perfluoroalkyl)phosphine oxides and tris(perfluoroalkyl)difluorophosphoranes with fluoride ion" in Zhurnal Obshchei Khimmi (1989), pp. 528–534, no month.*

Chemical Abstract for Jander et al. "Formation of trifluoromethyllated fluorophosphates by reaction of trimethyltrifluoromethyltin with phosphorus (V) fluoride" in Justus Liebigs Annalen der Chemie (1969), 726, pp. 19–24, no month.*

International Search Report, Aug. 2, 2002 for Application No. EP 01115786.

* cited by examiner

Primary Examiner—Susy Tsang-Foster
(74) Attorney, Agent, or Firm—Millen, White, Zelano & Branigan, P.C.

(57) ABSTRACT

The present invention relates to fluoroalkyl phosphates, to a process for the preparation, and to their use as conductive salts in batteries, capacitors, supercapacitors and galvanic cells.

14 Claims, 1 Drawing Sheet

FLUOROALKYL PHOSPHATES FOR USE IN ELECTROCHEMICAL CELLS

The present invention relates to fluoroalkyl phosphates, to a process for their preparation, and to their use as conductive salts in batteries, capacitors, supercapacitors and galvanic cells and to their use as a conductive salt in an electrolyte composition also containing a solvent.

BACKGROUND OF THE INVENTION

The spread of portable electronic equipment, such as, for example, laptop and palmtop computers, mobile telephones or video cameras, and thus also the demand for lightweight and high-performance batteries, has increased dramatically worldwide in recent years.

In view of this suddenly increased demand for batteries and the associated ecological problems, the development of rechargeable batteries with a long service life is of constantly increasing importance.

Lithium ion batteries and double layer capacitors with very high capacities (so-called super- or ultracapacitors) represent the current state of the art. In both systems, hydrolysis-sensitive and thermally unstable substances in the form of $LiPF_6$ or $N(C_2H_5)_4BF_4$ are currently used as conductive salt. In contact with moist air or with residual water from the solvents, HF can form rapidly. Besides the toxic properties, HF has a very adverse effect on the cycle behavior and thus on the performance of the electrochemical cells.

Alternatives which have been presented are imides, such as bis(trifluoromethylsulfonyl)imide or bis(pentafluoroethylsulfonyl)imide, or methanides, such as tris(trifluoromethylsulfonyl)methanide and derivatives thereof. These salts exhibit high positive-electrode stability and, with organic aprotic solvents, form solutions of high conductivity. However, the imides have the disadvantage that they do not sufficiently passivate the aluminum metal which functions as negative-electrode current collector in batteries. By contrast, methanides can only be prepared and purified at very great effort (Turowsky, Seppelt, Inorg. Chem., 1988, 2135). In addition, the electrochemical properties, such as oxidation stability and passivation of aluminum, are very highly dependent on the purity of the methanide.

SUMMARY OF THE INVENTION

An object of the invention was therefore to provide conductive salts which are electrochemically stable and are simple to prepare. A further object of the invention was also to extend or improve the service life and performance of batteries, capacitors, supercapacitors and galvanic cells.

Upon further study of the specification and appended claims, further objects and advantages of this invention will become apparent to those skilled in the art.

Surprisingly, these and other objects are achieved by the provision of fluoroalkyl phosphates of the general formula (I)

$$M^{n+}[PF_x(C_yF_{2y+1-z}H_z)_{6-x}]_n^- \qquad (I)$$

in which
  $1 \leq x \leq 6$,
  $1 \leq y \leq 8$,
  $0 \leq z \leq 2y+1$,
  $1 \leq n \leq 3$ and
  $M^{n+}$ is a monovalent to trivalent cation, in particular:

$NR^1R^2R^3R^4$,
$PR^1R^2R^3R^4$,
$P(NR^1R^2)_k R^3{}_m R^4{}_{4-k-m}$ (where k=1–4, m=0–3 and k+m$\leq$4),
$C(NR^1R^2)(NR^3R^4)(NR^5R^6)$,
$C(aryl)_3$, Rb or tropylium
where $R^1$ to $R^8$ are H, alkyl or aryl ($C_1$–$C_8$), which may be partially substituted by F, Cl or Br,
where $M^{n+}=Li^+$, $Na^+$, $Cs^+$, $K^+$ and $Ag^+$ are excluded.

Furthermore, the invention is drawn to a fluoroalkylphosphate of the formula $$M^{n+}[PF_x(C_yF_{2y+1-z}H_z)_{6-x}]_n^-$$

in which
  $1 \leq x < 6$,
  $1 \leq y \leq 8$,
  $0 \leq z \leq 2y+1$,
  $1 \leq n \leq 3$, and
  $M^{n+}$ is one of the following cations:
  $NR^1R^2R^3R^4$,
  $PR^1R^2R^3R^4$,
  $P(NR^1R^2)(NR^3R^4)(NR^5R^6)(NR^7R^8)$,
  $C(NR^1R^2)(NR^3R^4)(NR^5R^6)$,
  where $R^1$ to $R^8$ are H, $C_yF_{2y+1-z}H_z$ or an aromatic radical.

Preference is given to fluoroalkyl phosphates of the formula

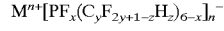

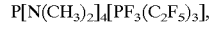

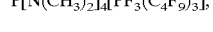

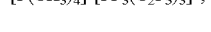

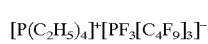

and

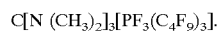

It has been found that the compounds according to the invention have very high electrochemical stability. The fluoroalkyl phosphates of the general formula (I) according to the invention can thus be employed, for example, in pure form and in the form of their mixtures, as conductive salts in primary and secondary batteries, capacitors, supercapacitors and galvanic cells. It is also possible for the fluoroalkyl phosphates according to the invention to be used as conductive salt together with further salts known to the person skilled in the art.

The fluoroalkyl phosphates according to the invention are preferably used in pure form as conductive salt, since in this way particularly good reproducibility of the electrochemical properties can be achieved.

The fluoroalkyl phosphates can be prepared starting from phosphoranes, which can be prepared by the process described in German patent application no. DE 196 411 38. From 0.01 to 4 molar, preferably from 0.5 to 3 molar, particularly preferably from 1.5 to 2.5 molar, solutions or suspensions of these phosphoranes or of the fluoroalkyl phosphates are prepared in solvents, preferably in organic aprotic solvents, particularly preferably selected from the group consisting of the carbonates, esters, ethers, nitriles, amides, ketones, sulfonic acid esters, sulfonamides, sulfoxides, phosphoric acid esters, phosphoranes, chloroalkanes and mixtures thereof. Preferred solvents are solvents or mixtures thereof which are directly suitable for use in a primary or secondary battery, a capacitor, a supercapacitor or a galvanic cell, such as, for example, dimethyl carbonate, diethyl carbonate, propylene carbonate, ethylene carbonate, ethyl methyl carbonate, methyl propyl carbonate, 1,2-dimethoxyethane, 1,2-diethoxyethane, methyl acetate, γ-butyrolactone, ethyl acetate, methyl propionate, ethyl propionate, methyl butyrate, ethyl butyrate, dimethyl sulfoxide, dioxolane, sulfolane, acetonitrile, acrylonitrile, tetrahydrofuran, 2-methyltetrahydrofuran or mixtures thereof.

For the reaction with fluoroalkyl phosphates, equimolar amounts or a slight excess of metal or nonmetal fluorides, chlorides, tetrafluoroborates or hexafluorophosphates, preferably selected from the group consisting of $[NR^1R^2R^3R^4]F$, $[NR^1R^2R^3R^4]Cl$, $[PR^1R^2R^3R^4]F$, $[PR^1R^2R^3R^4]Cl$, $[P(NR^1R^2)_4]F$, $[P(NR^1R^2)_4]Cl$, $[C(NR^1R^2)_3]Cl$ and $[C(NR^1R^2)_3]F$, if desired formulations thereof in solutions, are added. For the reaction with phosphoranes, $N(CH_3)_4F$, $N(C_2H_5)_4F$, $[P[(CH_3)_2]_4]F$ or $C[N(CH_3)_2]_3F$ is added in equimolar amounts or in a slight excess. The mixture is stirred in the liquid range, preferably at temperatures from about 0° C. to 50° C., particularly preferably at room temperature. It is stirred for from about 0.5 hour to 48 hours, preferably for from 2 to 12 hours. If the fluoroalkyl phosphate according to the invention is prepared by metathesis, the resultant by-product is separated off by cooling the reaction mixture followed by filtration. In the reactions in which no by-product is formed, the reaction mixture can be further employed directly.

The resultant electrolytes containing the fluoroalkyl phosphate(s) in solution are suitable for use in primary batteries, secondary batteries, capacitors, supercapacitors and galvanic cells and likewise represent subject matter of the present invention.

The concentration of the fluoroalkyl phosphate(s) according to the invention in these electrolytes is preferably from 0.01 to 4 mol/l, particularly preferably from 0.5 to 3 mol/l.

The invention also relates to primary batteries, secondary batteries, capacitors, supercapacitors and galvanic cells which contain at least one fluoroalkyl phosphate of the general formula (I) according to the invention and optionally further salts and/or additives. These further salts and additives may be selected from those known to the person skilled in the art, for example from Doron Aurbach: Nonaqueous Electrochemistry, Marc Dekker Inc., New York 1999; D.Linden: Handbook of Batteries, Second Edition, McGraw-Hill Inc., New York 1995, and G. Mamantov and A. I. Popov: Chemistry of Nonaqueous Solutions, Current Progress, VCH Verlagsgemeinschaft, Weinheim 1994. They are hereby incorporated by way of reference and are thus regarded as part of the disclosure.

The fluoroalkyl phosphates according to the invention can be used with conventional electrolytes. Examples of suitable electrolytes are those with conductive salts selected from the group consisting of $LiPF_6$, $LiBF_4$, $LiClO_4$, $LiAsF_6$, $LiCF_3SO_3$, $LiN(CF_3SO_2)_2$ and $LiC(CF_3SO_2)_3$, and mixtures thereof. The electrolytes may also comprise organic isocyanates (German patent application no. DE 199 44 603) for reducing the water content. Lithium complex salts of the general formula (German patent application no. DE 199 51 804)

in which:

x and y are 1, 2, 3, 4, 5 or 6

$M^{x+}$ is a metal ion

E is a Lewis acid selected from the group consisting of $BR^1R^2R^3$, $AlR^1R^2R^3$, $PR^1R^2R^3R^4R^5$, $AsR^1R^2R^3R^4R^5$ and $VR^1R^2R^3R^4R^5$, $R^1$ to $R^5$ are identical or different, are optionally bonded directly to one another by a single or double bond, and each, individually or together, are a halogen (F, Cl or Br), an alkyl or alkoxy radical ($C_1$ to $C_8$), which may be partially or fully substituted by F, Cl or Br, an aromatic ring, optionally bonded via oxygen, from the group consisting of phenyl, naphthyl, anthracenyl and phenanthrenyl, which may be unsubstituted or mono- to hexasubstituted by alkyl ($C_1$ to $C_8$) or F, Cl or Br, an aromatic heterocyclic ring, optionally bonded via oxygen, from the group consisting of pyridyl, pyrazyl and pyrimidyl, which may be unsubstituted or mono- to tetrasubstituted by alkyl ($C_1$ to $C_8$) or F, Cl or Br, and Z is $OR^6$, $NR^6R^7$, $CR^6R^7R^8$, $OSO_2R^6$, $N(SO_2R^6)(SO_2R^7)$, $C(SO_2R^6)(SO_2R^7)(SO_2R^8)$ or $OCOR^6$, where $R^6$ to $R^8$ are identical or different, are optionally bonded directly to one another by a single or double bond and are each, individually or together, hydrogen or as defined for $R^1$ to $R^5$, prepared by reacting a corresponding boron or phosphorus Lewis acid/solvent adduct with a lithium or tetraalkylammonium imide, methanide or triflate, may be present.

Borate salts (German patent application no. DE 199 59 722) of the general

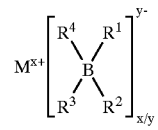

formula
in which:

M is a metal ion or tetraalkylammonium ion, x and y are 1, 2, 3, 4, 5 or 6, $R^1$ to $R^4$ are identical or different and are alkoxy or carboxyl radicals ($C_1$–$C_8$), which are optionally bonded directly to one another by a single or double bond, may also be present. These borate salts are prepared by reacting lithium tetraalkoxyborate or a 1:1 mixture of lithium alkoxide with a borate with a suitable hydroxyl or carboxyl compound in a ratio of 2:1 or 4:1 in an aprotic solvent.

Additives, such as silane compounds of the general formula $$SiR^1R^2R^3R^4$$

where $R^1$ to $R^4$ are H
$C_yF_{2y+1-z}H_z$
$OC_yF_{2y+1-z}H_z$
$OC(O)C_yF_{2y+1-z}H_z$
$OSO_2C_yF_{2y+1-z}H_z$
and
$1 \leq x \leq 6$
$1 \leq y \leq 8$ and
$0 \leq z \leq 2y+1$
and
$R^1$–$R^4$ are identical or different
and are an aromatic ring from the group consisting of phenyl and naphthyl, which may be unsubstituted or monosubstituted or polysubstituted by F, $C_yF_{2y+1-z}H_z$, $OC_yF_{2y+1-z}H_z$, $OC(O)C_yF_{2y+1-z}H_z$, $OSO_2C_yF_{2y+1-z}H_z$ or $N(C_nF_{2n+1-z}H_z)_2$, or
are a heterocyclic aromatic ring from the group consisting of pyridyl, pyrazyl and pyrimidyl, each of which may be monosubstituted or polysubstituted by F, $C_yF_{2y+1-z}H_z$, $OC_yF_{2y+1-z}H_z$, $OC(O)C_yF_{2y+1-z}H_z$, $OSO_2C_yF_{2y+1-z}H_z$ or $N(C_nF_{2n+1-z}H_z)_2$ (German patent application no. DE 100 276 26), may also be present.

The compounds according to the invention may also be employed in electrolytes comprising lithium fluoroalkyl phosphates of the following formula $$Li^+[PF_x(C_yF_{2y+1-z}H_z)_{6-x}]^-$$

in which
$1 \leq x \leq 5$
$3 \leq y \leq 8$
$0 \leq z \leq 2y+1$
and the ligands ($C_yF_{2y+1-z}H_z$) may be identical or different, with the exception of the compounds of the general formula $$Li^+[PF_a(CH_bF_c(CF_3)_d)_e]^-$$

in which a is an integer from 2 to 5, b=0 or 1, c=0 or 1, d=2 and
e is an integer from 1 to 4, with the provisos that b and c are not simultaneously each=0, and the sum a+e is equal to 6, and the ligands ($CH_bF_c(CF_3)_d$) may be identical or different (German patent application no. DE 100 089 55). The process for the preparation of lithium fluoroalkylphosphates is characterized in that at least one compound of the general formula $$H_mP(C_nH_{2n+1})_{3-m},$$
$$OP(C_nH_{2n+1})_3,$$
$$Cl_mP(C_nH_{2n+1})_{3-m},$$
$$F_mP(C_nH_{2n+1})_{3-m},$$
$$Cl_oP(C_nH_{2n+1})_{5-o},$$
$$F_oP(C_nH_{2n+1})_{5-o},$$

in each of which
$0 \leq m \leq 2$, $3 \leq n \leq 8$ and $0 \leq o \leq 4$, is fluorinated by electrolysis in hydrogen fluoride, the resultant mixture of fluorination products is separated by extraction, phase separation and/or distillation, and the resultant fluorinated alkylphosphorane is reacted with lithium fluoride in an aprotic solvent mixture with exclusion of moisture, and the resultant salt is purified and isolated by conventional methods.

The compounds according to the invention may also be employed in electrolytes which comprise salts of the formula $$Li[P(OR^1)_a(OR^2)_b(OR^3)_c(OR^4)_dF_e]$$

in which $0 < a+b+c+d \leq 5$ and $a+b+c+d+e = 6$, and $R^1$ to $R^4$, independently of one another, are alkyl, aryl or heteroaryl radicals, where at least two of $R^1$ to $R^4$ may be linked directly to one another via a single or double bond (German patent application no. DE 100 16 801). The compounds are prepared by reacting phosphorus (V) compounds of the general formula $$P(OR^1)_a(OR^2)_b(OR^3)_c(OR^4)_dF_e$$

in which $0 < a+b+c+d \leq 5$ and $a+b+c+d+e = 5$, and $R^1$ to $R^4$ are as defined above, with lithium fluoride in the presence of an organic solvent.

It is also possible for ionic liquids of the general formula $$K^+A^-$$

in which:

$K^+$ is a cation selected from the group consisting of

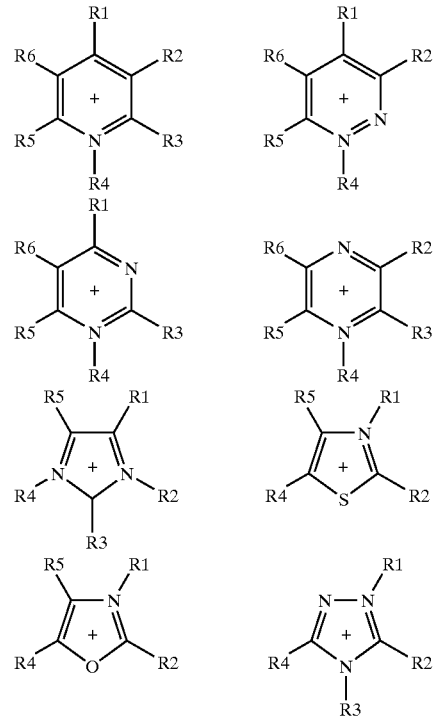

where $R^1$ to $R^5$ are identical or different, are optionally bonded directly to one another by a single or double bond, and each, individually or together, have the following meaning:

H, halogen, an alkyl radical ($C_1$ to $C_8$), which may be partially or fully substituted by further groups, F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, where $1<n<6$ and $0<x\leq13$, and $A^-$ is an anion selected from the group consisting of $$[B(OR^1)_n(OR^2)_m(OR^3)_o(OR^4)_p]^-$$

where $0\leq n, m, o, p\leq4$, and $m+n+o+p=4$, where $R^1$ to $R^4$ are different or are identical in pairs, are optionally bonded directly to one another by a single or double bond and are each, individually or together, an aromatic ring from the group consisting of phenyl, naphthyl, anthracenyl and phenanthrenyl, which may be unsubstituted or monosubstituted or polysubstituted by $C_nF_{(2n+1-x)}H_x$, where $1<n<6$ and $0<x\leq13$, or halogen (F, Cl or Br), an aromatic heterocyclic ring from the group consisting of pyridyl, pyrazyl and pyrimidyl, which may be unsubstituted or monosubstituted or polysubstituted by $C_nF_{(2n+1-x)}H_x$, where $1<n<6$ and $0<x\leq13$, or halogen (F, Cl or Br), an alkyl radical ($C_1$ to $C_8$), which may be partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, where $1<n<6$ and $0<x\leq13$, or $OR^1$ to $OR^4$ individually or together are an aromatic or aliphatic carboxyl, dicarboxyl, oxysulfonyl or oxycarbonyl radical, which may be partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$ or $C_nF_{(2n+1-x)}H_x$, where $1<n<6$ and $0<x\leq13$ (German patent application no. DE 100 265 65), to be present in the electrolyte. It is also possible for ionic liquids $K^+A^-$ where $K^+$ is as defined above and $A^-$ is an anion selected from the group consisting of $$[PF_x(C_yF_{2y+1-z}H_z)_{6-x}]^-$$

and $1\leq x<6$ $1\leq y\leq8$ and $0\leq z\leq2y+1$ to be present (GERMAN PATENT APPLICATION NO. DE 100 279 95).

The compounds according to the invention may also be present in electrolytes comprising compounds of the following formula:

$$NR^1R^2R^3$$

in which $R^1$ and $R^2$ are H, $C_yF_{2y+1-z}H_z$ or $(C_nF_{2n-m}H_m)X$, where X is an aromatic or heterocyclic radical, and $R^3$ is $(C_nF_{2n-m}H_m)Y$, where Y is a heterocyclic radical, or $(C_oF_{2o-p}H_p)Z$, where Z is an aromatic radical, and where n, m, o, p, y and z satisfy the following conditions:

$0\leq n\leq6$, $0\leq m\leq2n$, $2\leq o\leq6$, $0\leq p\leq2o$, $1\leq y\leq8$, and $0\leq z\leq2y+1$, for reducing the acid content in aprotic electrolyte systems in electro-chemical cells.

The electrolyte may also comprise a mixture of a) at least one lithium fluoroalkyl phosphate salt of the general formula $$Li^+[PF_x(C_yF_{2y+1-z}H_z)_{6-x}]^-$$

in which $1\leq x\leq5$ $1\leq y\leq8$, and $0\leq z\leq2y+1$ and the ligands ($C_yF_{2y+1-z}H_z$) are in each case identical or different, and b) at least one polymer (German Patent Application No. DE 100 58 264).

The electrolyte may also comprise tetrakisfluoroalkyl borate salts of the general formula $$M^{n+}([BR_4]^-)_n$$

in which $M^{n+}$ is a monovalent, divalent or trivalent cation, the ligands R are in each case identical and are ($C_xF_{2x+1}$), where $1\leq x\leq8$, and n=1, 2 or 3 (German Patent Application No. DE 100 558 11). The process for the preparation of tetrakis-fluoroalkyl borate salts is characterized in that at least one compound of the general formula $M^{n+}([B(CN)_4]^-)_n$, in which $M^{n+}$ and n are as defined above, is fluorinated by reaction with at least one fluorinating agent in at least one solvent, and the resultant fluorinated compound is purified and isolated by conventional methods.

The electrolyte may also comprise borate salts of the general formula $$M^{n+}[BF_x(C_yF_{2y+1-z}H_z)_{4-x}]_n^-$$

in which:

$1<x<3$, $1\leq y\leq8$ and $0\leq z\leq2y+1$, and

M is a monovalent to trivalent cation ($1\leq n\leq3$), apart from potassium and barium, in particular:

Li, $NR^1R^2R^3R^4$, $PR^5R^6R^7R^8$, $P(NR^5R^6)_kR^7{}_mR^8{}_{4-k-m}$ (where k=1–4, m=0–3 and k+m$\leq$4), or $C(NR^5R^6)(NR^7R^8)(NR^9R^{10})$, where $R^1$ to $R^4$ are $C_yF_{2y+1-z}H_z$ and $R^5$ to $R^{10}$ are H or $C_yF_{2y+1-z}H_z$, or an aromatic heterocyclic cation, in particular a nitrogen- and/or oxygen- and/or sulfur-containing aromatic heterocyclic cation (German patent application no. DE 101 031 89). The process for the preparation of these compounds is characterized in that a) $BF_3$/solvent complexes are reacted 1:1 with alkyl-lithium with cooling, the majority of the solvent is removed after slow warming, and the solid is subsequently filtered off and washed with a suitable solvent, or b) lithium salts in a suitable solvent are reacted 1:1 with B(CF$_3$)F$_3$ salts, the mixture is stirred at elevated temperature, the solvent is removed, aprotic non-aqueous solvents, preferably solvents which are used in electrochemical cells, are added to the reaction mixture, and the mixture is dried, or c) B(CF$_3$)F$_3$ salts are reacted 1:1 to 1:1.5 with lithium salts in water at elevated temperature and heated at the boiling point for from 0.5 to 2 hours, the water is removed, aprotic non-aqueous solvents, preferably solvents which are used in electrochemical cells, are added to the reaction mixture and the mixture is dried.

The compounds according to the invention may be present in electrolytes which comprise fluoroalkyl phosphate salts (German patent application no. DE 10109032) of the formula

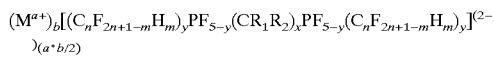

in which

M$^{a+}$ is a monovalent, divalent or trivalent cation, a=1, 2 or 3, b=2 for a=1, b=2 for a=3, b=1 for a=2 and in each case $1 \leq n \leq 8$, $0 \leq m \leq 2$ for n–1 or 2, $0 \leq m \leq 4$ for $3 \leq n \leq 8$, $1 \leq x \leq 12$, $0 \leq y \leq 2$, where R$_1$ and R$_2$ are in each case identical or different and are selected from the group consisting of fluorine, hydrogen, alkyl, fluoroalkyl and perfluoroalkyl substituents, and where in each case the substituents (C$_n$F$_{2n+1-m}$H$_m$) are identical or different. These compounds are prepared by reacting at least one fluoro-α,ω-bis(alkylfluorophosphorano)alkane with at least one fluoride salt of the general formula (M$^{a+}$) [F$^-$]$_a$, in which (M$^{a+}$) and a are as defined above, in solution to give a fluoroalkyl phosphate salt, and, if desired, purifying and/or isolating the latter by conventional methods.

The compounds according to the invention can be used in electrolytes for electrochemical cells containing positive-electrode material consisting of coated metal cores selected from the group consisting of Sb, Bi, Cd, In, Pb, Ga and tin or alloys thereof (German patent application no. DE 100 16 024). The process for the preparation of this positive-electrode material is characterized in that a) a suspension or sol of the metal or alloy core in urotropin is prepared, b) the suspension is emulsified with C$_5$–C$_{12}$-hydrocarbons, c) the emulsion is precipitated onto the metal or alloy cores, and d) the metal hydroxides or oxyhydroxides are converted into the corresponding oxide by heating the system.

The compounds according to the invention can also be employed in electrolytes for electrochemical cells having negative electrodes made from common lithium intercalation and insertion compounds, but also with negative-electrode materials consisting of lithium mixed oxide particles coated with one or more metal oxides (German patent application no. DE 199 22 522). They may also consist of lithium mixed oxide particles coated with one or more polymers (German patent application no. DE 199 46 066). The compounds according to the invention may likewise be employed in systems having negative electrodes consisting of lithium mixed oxide particles with one or more coatings of alkali metal compounds and metal oxides (DE 100 14 884). The process for the production of these materials is characterized in that the particles are suspended in an organic solvent, an alkali metal salt compound suspended in an organic solvent is added, metal oxides dissolved in an organic solvent are added, a hydrolysis solution is added to the suspension, and the coated particles are subsequently filtered off, dried and calcined. The compounds according to the invention can likewise be employed in systems comprising positive-electrode materials with doped tin oxide (German patent application no. DE 100 257 61). This positive-electrode material is prepared by a) adding urea to a tin chloride solution, b) adding urotropin and a suitable doping compound to the solution, c) emulsifying the resultant sol in petroleum ether, d) washing the resultant gel and removing the solvent by suction, and e) drying and heating the gel.

The compounds according to the invention can likewise be employed in systems comprising positive-electrode materials with reduced tin oxide (German patent application no. DE 100 257 62). This positive-electrode material is prepared by a) adding urea to a tin chloride solution, b) adding urotropin to the solution, c) emulsifying the resultant sol in petroleum ether, d) washing the resultant gel and removing the solvent by suction, e) drying and heating the gel, and f) exposing the resultant SnO$_2$ to a reducing gas stream in an aeratable oven.

The fluoroalkyl phosphates according to the invention have the advantage of being electrochemically stable. This property enables conductive salts and electrolytes comprising the compounds according to the invention to be employed in batteries, capacitors, supercapacitors and galvanic cells. They can be employed in such uses in a manner analogous to known conductive salts or electrolytes but exhibiting the stated advantages. For example, they preferably provide a positive-electrode stability of greater than 4V, more preferably greater than 5V.

The entire disclosure of all applications, patents and publications, cited above, and of corresponding German application No. 10038858.2, filed Aug. 4, 2000 is hereby incorporated by reference.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

Example 1

Preparation of N(C$_2$H$_5$)$_4$[PF$_3$(C$_2$F$_5$)$_3$] via Li[PF$_3$(C$_2$F$_5$)$_3$]

Equimolar amounts of N(C$_2$H$_5$)$_4$X (X=F or Cl) in methylene chloride are added to a 1.5 to 2.5 molar solution of Li[PF$_3$(C$_2$F$_5$)$_3$]. The solution is stirred at room temperature for a number of hours, during which a slight sediment of LiX forms. The reaction mixture is then held at from −30° C. to −10° C. for a further 2 hours, and the resultant precipitate is filtered off at from −30° C. to −10° C. under reduced pressure. The solvent is removed by distillation. After subsequent drying at 100° C. under reduced pressure, the product can be obtained in the form of colorless granules.

$^{19}$F-NMR spectroscopy (CD$_3$CN; standard: CCl$_3$F):
−43.6 dm (1F)
−79.7 m (3F)
−81.3 m (6F)
−87.0 dm (2F)
−115.3 m (4F)
−115.7 m (2F)

Example 2

Preparation of N(CH$_3$)$_4$[PF$_3$(C$_2$F$_5$)$_3$] via PF$_2$(C$_2$F$_5$)$_3$

An equimolar amount of N(CH$_3$)$_4$F is added at −40° C. to 10 g of PF$_2$(C$_2$F$_5$)$_3$ (prepared in accordance with German patent application no. DE 198 466 36) in dichloromethane. The mixture is stirred for a number of hours and warmed to room temperature. The solvent is removed by distillation, and N(CH$_3$)$_4$[PF$_3$(C$_2$F$_5$)$_3$] is isolated.

$^{19}$ F-NMR spectroscopy (CD$_3$CN; standard: CCl$_3$F):
−44.0 dm (1F)
−80.0 m (3F)
−82 m (6F)
−87.5 dm (2F)
−115.8 m (4F)
−116.2 m (2F)

Example 3

Preparation of N(CH$_3$)$_4$[PF$_3$(C$_4$F$_9$)$_3$] via PF$_2$(C$_4$F$_9$)$_3$

The preparation is carried out analogously to Example 2 starting from PF$_2$(C$_4$F$_9$)$_3$. The cation source employed is N(CH$_3$)$_4$F.

Example 4

Preparation of P[N(CH$_3$)$_2$]$_4$[PF$_3$(C$_2$F$_5$)$_3$] and P[N(CH$_3$)$_2$]$_4$[PF$_3$(C$_4$F$_9$)$_3$]

The preparation is carried out analogously to Example 2. The cation source employed is P[N(CH$_3$)$_2$]$_4$F.

Example 5

Preparation of P[N(CH$_3$)$_2$]$_4$[PF$_3$(C$_4$F$_9$)$_3$] and P[N(CH$_3$)$_2$]$_4$[PF$_3$(C$_2$F$_5$)$_3$]

The preparation is carried out analogously to Example 1. The cation source employed is P[N(CH$_3$)$_2$]$_4$Cl.

Example 6

Preparation of C[N(CH$_3$)$_2$]$_3$[PF$_3$(C$_2$F$_5$)$_3$] and C[N(CH$_3$)$_2$]$_3$[PF$_3$(C$_4$F$_9$)$_3$]

The preparation is carried out analogously to Example 1. The cation source employed is C[N(CH$_3$)$_2$]$_3$Cl.

Example 7

Electrochemical Stability of the Electrolytes

In a measurement cell with stainless steel, platinum or gold working electrode, lithium counterelectrode and lithium reference electrode, in each case 5 cyclic voltammograms were recorded one after the other. To this end, the potential was firstly increased starting from the rest potential at a rate of 10 mV/s or 20 mV/s to 6 V against Li/Li$^+$, and then moved back to the rest potential. In order to be able to utilize the highest possible electrochemical window, a 1:1 mixture of EC and DMC was used as solvent.

All electrolytes here exhibit a positive-electrode stability of greater than 5 V. FIG. 1 shows this in a representative manner for the electrolyte comprising [PF$_3$(C$_2$F$_5$)$_3$]$^-$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Figure 1:
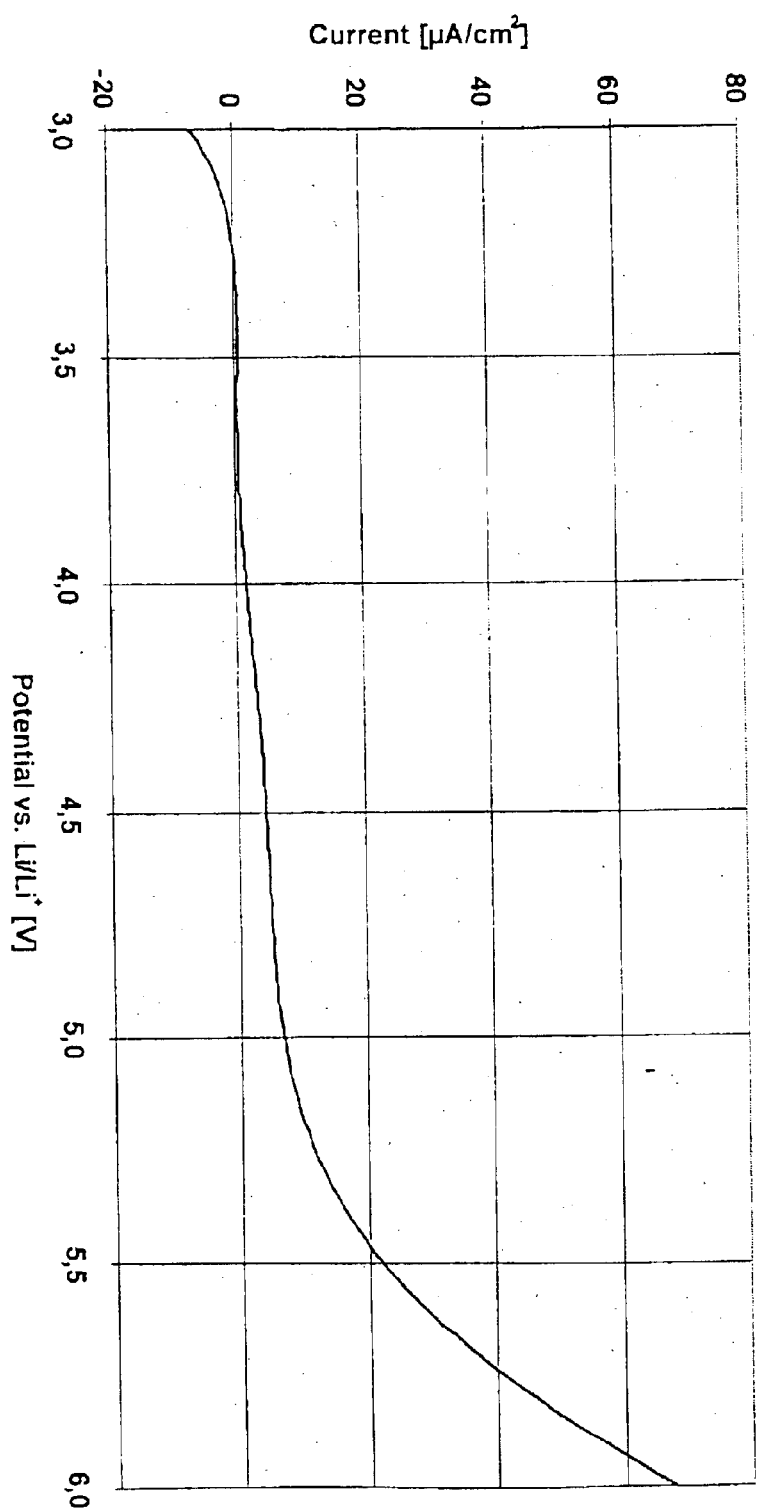
FIG. 1 is a graphic representation of the oxidation stability results from Example 7.

What is claimed is:

1. A fluoroalkyl phosphate of the formula (I)

$$M^{n+}[PF_x(C_yF_{2y+1-z}H_z)_{6-x}]_n^-$$ (I)

in which
$1 \leq x < 6$,
$1 \leq y \leq 8$,
$0 \leq z \leq 2y+1$,
$1 \leq n \leq 3$, and
M$^{n+}$ is one of the following cations:
NR$^1$R$^2$R$^3$R$^4$,
PR$^1$R$^2$R$^3$R$^4$,
P(NR$^1$R$^2$)(NR$^3$R$^4$)(NR$^5$R$^6$)(NR$^7$R$^8$),
C(NR$^1$R$^2$)(NR$^3$R$^4$)(NR$^5$R$^6$),
where R$^1$ to R$^8$ are H, C$_y$F$_{2y+1-z}$H$_z$ or an aromatic radical.

2. A fluoroalkyl phosphate according to claim 1, which is:
a) [N(CH$_3$)$_4$][PF$_3$(C$_4$F$_9$)$_3$],
b) [N(C$_2$H$_5$)$_4$][PF$_3$(C$_2$F$_5$)$_3$],
c) [P(C$_2$H$_5$)$_4$]$^+$[PF$_3$(C$_2$F$_5$)$_3$]$^-$, or
d) [P(C$_2$H$_5$)$_4$]$^+$[PF$_3$[C$_4$F$_9$]$_3$]$^-$.

3. A fluoroalkyl phosphate according to claim 1, which is:
a) N(C$_2$H$_5$)$_4$[PF$_3$(C$_2$F$_5$)$_3$],
b) N(CH$_3$)$_4$[PF$_3$(C$_4$F$_9$)$_3$],
c) P[N(CH$_3$)$_2$]$_4$[PF$_3$(C$_2$F$_5$)$_3$],
d) P[N(CH$_3$)$_2$]$_4$[PF$_3$(C$_4$F$_9$)$_3$],
e) [P(CH$_3$)$_4$]$^+$[PF$_3$(C$_2$F$_5$)$_3$]$^-$,
f) [P(CH$_3$)$_4$]$^+$[PF$_3$[C$_4$F$_9$]$_3$]$^-$,
g) C[N(CH$_3$)$_2$]$_3$[PF$_3$(C$_2$F$_5$)$_3$]or
h) C[N (CH$_3$)$_2$]$_3$[PF$_3$(C$_4$F$_9$)$_3$].

4. A process for preparing a fluoroalkyl phosphate according to claim 1, which comprises reacting a phosphorane with a fluoride salt or reacting a fluoroalkyl phosphate with an M$^{n+}$ salt with fluoride, chloride, tetrafluoroborate, and hexafluorophosphate in a solvent.

5. The process of claim 4, wherein the solvent is an organic aprotic solvent.

6. A process for the preparation of a fluoroalkyl phosphate according to claim 4, which comprises reacting a fluoroalkyl phosphate with $[NR^1R^2R^3R^4]X$, $[P(NR^1R^2)_4]X$, $[PR^1R^2R^3R^4]X$ or $[C(NR^1R^2)_3]X$, where $X=F^-$, $Cl^-$, $BF_4^-$ or $PF_6^-$, and $R^{1-4}$ are H, $C_yF_{2y+1-z}H_z$ or an aromatic radical.

7. A process for the preparation of a fluoroalkyl phosphate according to claim 4, which comprises reacting a phosphorane with $N(CH_3)_4F$, $N(C_2H_5)_4F$, $[P[N(CH_3)_2]_4]F$ or $C[N(CH_3)_2]_3F$.

8. A process for the preparation of a fluoroalkyl phosphate according to claim 3, which comprises reacting a fluorinated alkylphosphorane in a solvent or solvent mixture which is directly suitable for use in a primary or secondary battery, a capacitor, a supercapacitor or a galvanic cell.

9. A process for the preparation of a fluoroalkyl phosphate according to claim 5, wherein the organic aprotic solvent is selected from the group consisting of the carbonates, esters, ethers, nitriles, amides, ketones, sulfonic acid esters, sulfonamides, sulfoxides, phosphoric acid esters, phosphoranes, chloroalkanes and mixtures thereof.

10. A process according to claim 4, wherein the solvent employed is dimethyl carbonate, diethyl carbonate, propylene carbonate, ethylene carbonate, ethyl methyl carbonate, methyl propyl carbonate, 1,2-dimethoxyethane, 1,2-diethoxyethane, methyl acetate, γ-butyrolactone, ethyl acetate, methyl propionate, ethyl propionate, methyl butyrate, ethyl butyrate, dimethyl sulfoxide, dioxolane, sulfolane, acetonitrile, acrylonitrile, tetrahydrofuran, 2-methyltetrahydrofuran or mixtures thereof.

11. A primary battery, secondary battery, capacitor, supercapacitor or galvanic cell, which contains as a conductive salt, at least one fluoroalkyl phosphate of claim 1, optionally also in combination with further salts.

12. An electrolyte for a primary battery, secondary battery, capacitor, supercapacitor or galvanic cell comprising at least one fluoroalkyl phosphate according to claim 1 in solution.

13. An electrolyte according to claim 12, wherein the concentration of the fluoroalkyl phosphate(s) in the electrolyte is from 0.5 to 3 mol/l.

14. An electrolyte according to claim 12, wherein the concentration of the fluoroalkyl phosphate(s) in the electrolyte is from 0.01 to 4 mol/l.

* * * * *